(12) United States Patent
Haun et al.

(10) Patent No.: US 11,185,428 B2
(45) Date of Patent: Nov. 30, 2021

(54) PROSTHETIC EXTERNAL FIXATION ASSEMBLY FOR POST-AMPUTEE AMBULATION

(71) Applicants: Dennis G. Haun, Fallston, MD (US); Johnnie Loveday, Fallston, MD (US); Christopher Bibbo, Baltimore, MD (US)

(72) Inventors: Dennis G. Haun, Fallston, MD (US); Johnnie Loveday, Fallston, MD (US); Christopher Bibbo, Baltimore, MD (US)

(73) Assignee: POST-OP INNOVATIONS, INC., Fallston, MD (US)

(*) Notice: Subject to any disclaimer, the term of this patent is extended or adjusted under 35 U.S.C. 154(b) by 182 days.

(21) Appl. No.: 16/589,472

(22) Filed: Oct. 1, 2019

(65) Prior Publication Data

US 2020/0038202 A1    Feb. 6, 2020

Related U.S. Application Data

(62) Division of application No. 15/961,166, filed on Apr. 24, 2018, now Pat. No. 10,485,679.

(60) Provisional application No. 62/489,122, filed on Apr. 24, 2017.

(51) Int. Cl.
| | |
|---|---|
| *A61F 2/60* | (2006.01) |
| *A61F 2/76* | (2006.01) |
| *A61B 17/62* | (2006.01) |
| *A61F 2/80* | (2006.01) |

(Continued)

(52) U.S. Cl.
CPC .............. *A61F 2/60* (2013.01); *A61B 17/62* (2013.01); *A61F 2/76* (2013.01); *A61F 2/80* (2013.01); *A61B 17/6425* (2013.01); *A61F 2002/502* (2013.01); *A61F 2002/5018* (2013.01);

(Continued)

(58) Field of Classification Search
CPC ..... A61F 2/60; A61F 2/78; A61F 2/80; A61B 17/60; A61B 17/62; A61B 17/64; A61B 17/645
See application file for complete search history.

(56) References Cited

U.S. PATENT DOCUMENTS

2014/0121783 A1* 5/2014 Alley ....................... A61F 2/80
623/33

* cited by examiner

*Primary Examiner* — Eduardo C Robert
*Assistant Examiner* — Christina NegrelliRodriguez
(74) *Attorney, Agent, or Firm* — Royal W. Craig; Gordon Feinblatt LLC

(57) ABSTRACT

A fixation assembly for attaching a prosthetic leg and foot combination directly to an external ring fixation assembly via a protective socket, and yet allow full adjustment of length and offset, protection of the residual stump when in use, and quick-disconnect of the socket when not in use. The device is meant for use with any existing external fixation ring assembly for fixation to a femur or tibia, and any prosthetic leg/foot combination. The fixation assembly generally includes a molded concave socket having a mounting base at its apex for mounting the prosthetic leg/foot, an articulating ring adjustably attached to the socket, and a plurality of struts there between. Each strut has a first locking pivot joint at one end pivotally attached to the articulating ring and a second locking pivot joint at an opposing end pivotally attached to the rim of the socket. The articulating ring is removably attached to the external ring fixation assembly by a plurality of detent pins for releasable attachment.

20 Claims, 4 Drawing Sheets

(51) Int. Cl.
*A61B 17/64* (2006.01)
*A61F 2/50* (2006.01)
(52) U.S. Cl.
CPC ............ *A61F 2002/5083* (2013.01); *A61F 2002/5084* (2013.01); *A61F 2002/607* (2013.01)

PROSTHETIC EXTERNAL FIXATION ASSEMBLY FOR POST-AMPUTEE AMBULATION

CROSS-REFERENCE TO RELATED APPLICATION(S)

The present application derives priority from U.S. application Ser. No. 15/961,166 filed 24 Apr. 2018, which in turn derives priority from provisional application Ser. No. 62/489,122 filed Apr. 24, 2017.

BACKGROUND OF THE INVENTION

1. Field of the Invention

The present invention relates generally to prosthetics and more particularly, to a prosthetic leg mounting system for external ring fixators for faster post-operative ambulation.

2. Description of the Background

When a patient encounters a traumatic injury to his or her lower limb, external ring fixators are often used as a method of immobilizing leg and other limb bones to allow a fracture to heal. They utilize two or more rings with radial pins or screws that are placed into the bone on all sides of the fracture. As the bones mend back together, the external fixator can be adjusted such that the bones remain in an optimal position during the healing process.

For example, U.S. Pat. No. 7,306,601 to McGrath et al. (Quantum Medical Concepts, Inc.) issued Dec. 11, 2007 shows a typical external ring fixation system.

It is also known that the healing process can be accelerated by getting the patient up and moving to increase circulation, which helps with healing. For this reason some patients have an additional ring, or footplate, attached beneath their foot that allows them to bear weight and ambulate. This additional ring or foot ring typically attaches with four (or more) threaded rods that are secured with multiple nuts above and below each ring.

For example, United States Patent Application 20150112339 by Lindahl et al. (Aalto University Foundation) published Apr. 23, 2015 shows an external ring fixator with attached shoe for controlling ankle movement.

U.S. Pat. No. 8,192,434 to Huebner et al. (Quantum Medical Concepts LLC) issued Jun. 5, 2012 shows an external ring fixation assembly with a foot-supporting plate.

U.S. Pat. No. 8,323,282 to Taylor issued Dec. 4, 2012 shows a walking plate for an orthopedic ring-fixator.

U.S. Pat. No. 9,381,129 to Vicik issued Jul. 5, 2016 (MGV Enterprises, Inc) shows an external ring-fixator and auxiliary support having a quick-release mechanism.

For the very same reasons, it is likewise desirable to get amputates ambulating as soon as possible after their procedures, but this is more difficult and less common. This is noted in the "Lengthening of Tibia . . . " article by Garrison and Rozbruch (2016) where the authors attached a prosthetic leg to a weight-bearing external ring fixator to allow for early weight bearing and exercising. In this case, the prosthesis was simply screwed to a bottom ring.

What is needed is a prosthetic external ring fixation assembly that facilitates immediate attachment of a prosthetic leg and foot for immediate post-amputee ambulation to get the patient up and moving, increase circulation, and expedite healing.

SUMMARY OF THE INVENTION

In accordance with the foregoing it is an object of the invention to provide a prosthetic leg mounting system for external ring fixators that facilitates immediate attachment of a prosthetic leg and foot for immediate post-amputee ambulation to get the patient up and moving, increase circulation, and expedite healing.

The foregoing and other objects are accomplished with an improved prosthetic external ring fixation assembly for quick-connect adjustable attachment of a prosthetic leg for immediate post-amputee ambulation. The device is configured for use with an existing external fixation ring assembly for fixation to a femur or tibia, and an existing prosthetic leg and foot combination of choice. The assembly generally includes an articulating ring adjustably-attached to a concave socket by locking-ball-joint struts, and quick-connect pins insertable through the external ring fixation assembly and into receptacles on the articulating ring for releasable attachment. The socket has an open end surrounded by a reinforcing ring, and a closed end at its apex with a mounting base for mounting the prosthetic leg/foot. The quick-connect mechanism is a plurality of detent pins that allow releasable mounting of the socket/articulating ring to the external fixation ring assembly via the reinforcing ring.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

Reference will now be made in detail to preferred embodiments of the present invention, examples of which are illustrated in the accompanying drawings. Wherever possible, the same reference numbers will be used throughout the drawings to refer to the same or like parts.

The present invention is an improved prosthetic external ring fixation assembly for quick-connect adjustable attachment of a prosthetic leg post-amputee ambulation as soon as possible after their procedures.

Figure 1:
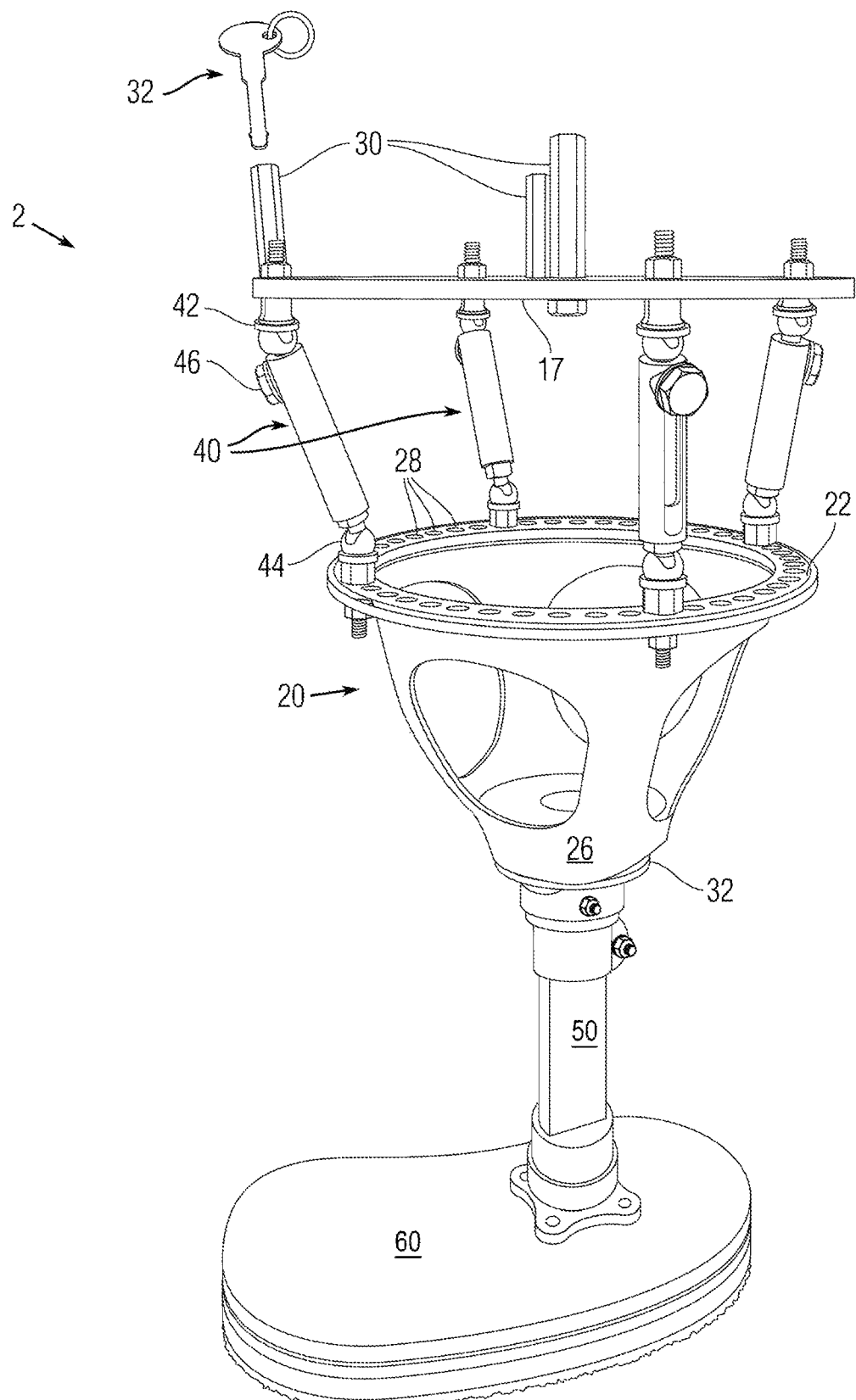
FIG. 1 is a perspective illustration of a system for mounting a prosthetic leg to an external ring fixation assembly according to the invention.
Figure 2:
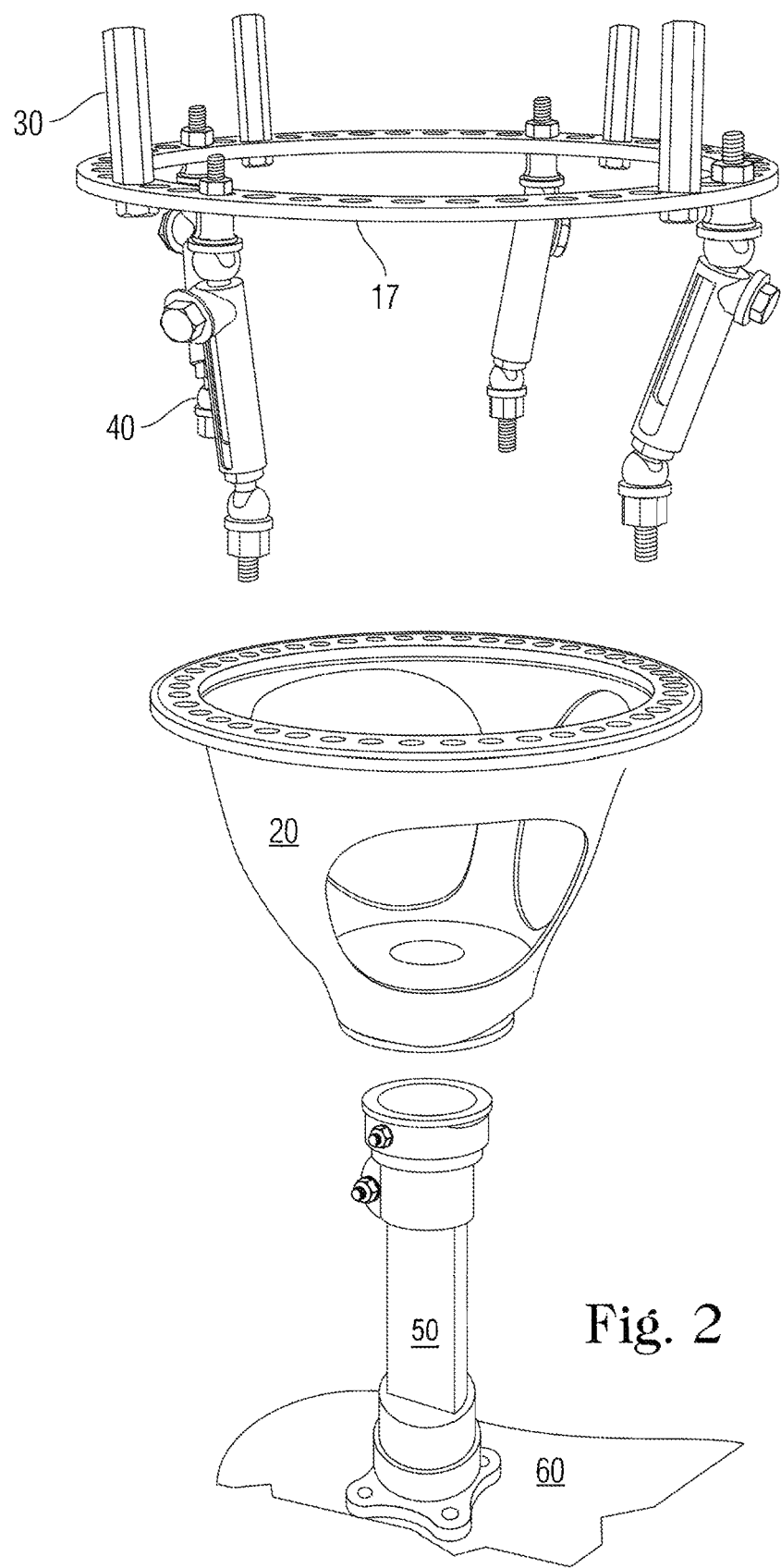
FIG. 2 is perspective exploded illustration of the system 2 of FIG. 1.
Figure 4:
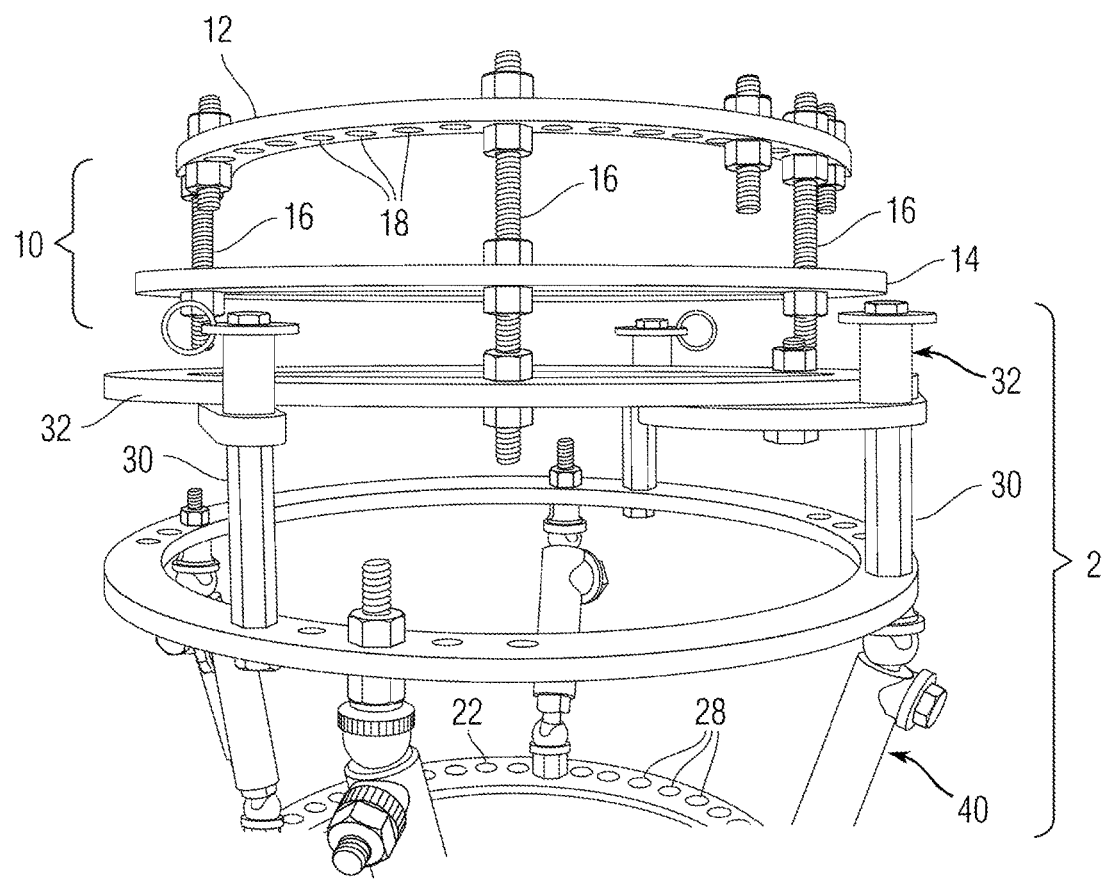
FIG. 4 is a close-up perspective illustration of the system 2 as in FIG. 3 connected to an external ring fixator 10.

FIGS. 1-2 are perspective illustrations of the system 2 for mounting a prosthetic leg to an external ring fixation assembly according to the invention. FIG. 4 shows the system 2 attached to an external ring fixation assembly 10.

The system 2 is configured for quick-release attachment to the external fixation ring assembly 10 (FIG. 4) for fixation to the thigh bone (femur) or to the tibia (shinbone). The external fixation ring assembly 10 is a conventional component used to stabilize bone and soft tissues at a distance from the operative or injury focus. The external fixation ring assembly 10 includes at least one ring, in this case two rings 12, 14 connected to one another via threaded struts 16. The struts 16 may, for example, be received in openings 18 of the rings 12, 14 and screwed thereto. The struts 16 determine the spacing and/or angular disposition of the rings 12, 14 by holding them in a substantially fixed relative disposition. The struts 16 may be arranged around the rings 12, 14 as desired, preferably at 0, 45, 90 and 135 degree equiangular increments although three to six struts may be used as a matter of design choice. Each strut 16 may be adjustable in length and/or angular disposition relative to the rings 12, 14. In some commercial embodiments, each strut 16 may have a length-adjustment capability that allows the length of the strut 16 to be adjusted telescopically (and then locked at length). The rings 12, 14 may be connected to bone in a conventional manner via any suitable pins, rods, and/or screws.

The system 2 includes a mounting assembly 20 comprising an articulating ring 17 pivotally attached to a reducer 20, the articulating ring 17 being attached to the lowermost ring 14 (seen in FIG. 4) of external fixation ring assembly 10 by a plurality of spacers 30 that accept quick-connect pins 32 for removable connection on one side to the lowermost ring 14. The quick-connect pins 32 are preferably detent lock pop-and-plunger pins, and most preferably button-handle lock pins, 2", ¼" diameter.

The articulating ring 17 is attached to the reducer 20 by a plurality (preferably four) unidirectional-pivoting length adjustable struts 40. Each strut 40 is pivotally-connected to the articulating ring 16 at one end by a first unidirectional pivot joint 42, and is pivotally-connected to a reinforcing ring 22 at the rim of reducer 20 by a second unidirectional pivot joint 44. Each strut 40 can be independently lengthened or shortened and fixed in length and/or orientation by a locking screw 46. The struts 40 preferably include threaded distal ends for attachment, and are secured by nuts at one end in openings 18 of the lower ring 14 and screwed thereto. The struts 40 are likewise secured by nuts at the other end in openings 28 of the reinforcing ring 22 at the rim of reducer 20. The struts 40 may each be a Tru-Lock™ Rapid Strut manufactured by Orthofix SRL. This configuration allows for limited spatial adjustment (position, orientation and fixation) of the articulating ring 16 (and external fixation ring assembly 10) relative to the reducer 20 within a three-dimensional frame of reference.

The other side of reducer 20 is configured with a prosthetic mounting plate 32. The mounting plate 32 may vary depending on the desired prosthetic. As an example, the mounting plate 32 may be a 4-hole pyramid adapter generally including a keyed male pin for docking in a conventional pyramid receptacle, the pin capable of being locked in position with set screws. The docking pin/receptacle combination further allows mounting a prosthetic leg 50 and foot 60 thereto, allowing for early weight bearing and exercising. The reducer 20 also protects the residual stump post-amputation. The foot 60 may be a foreshortened prostheses ("stubby") such as shown and described in U.S. Pat. No. 9,301,859 to Haun, or any other suitable foot, and an exemplary receptacle in U.S. Pat. No. 8,252,066 to Haun or other suitable receptacle.

The foregoing system 2 is quickly attachable, fully adjustable, and allows the amputee patient to remain active and ambulatory with minimal assistive devices, improving circulation and healing as well as psychological advantages.

Figure 3:
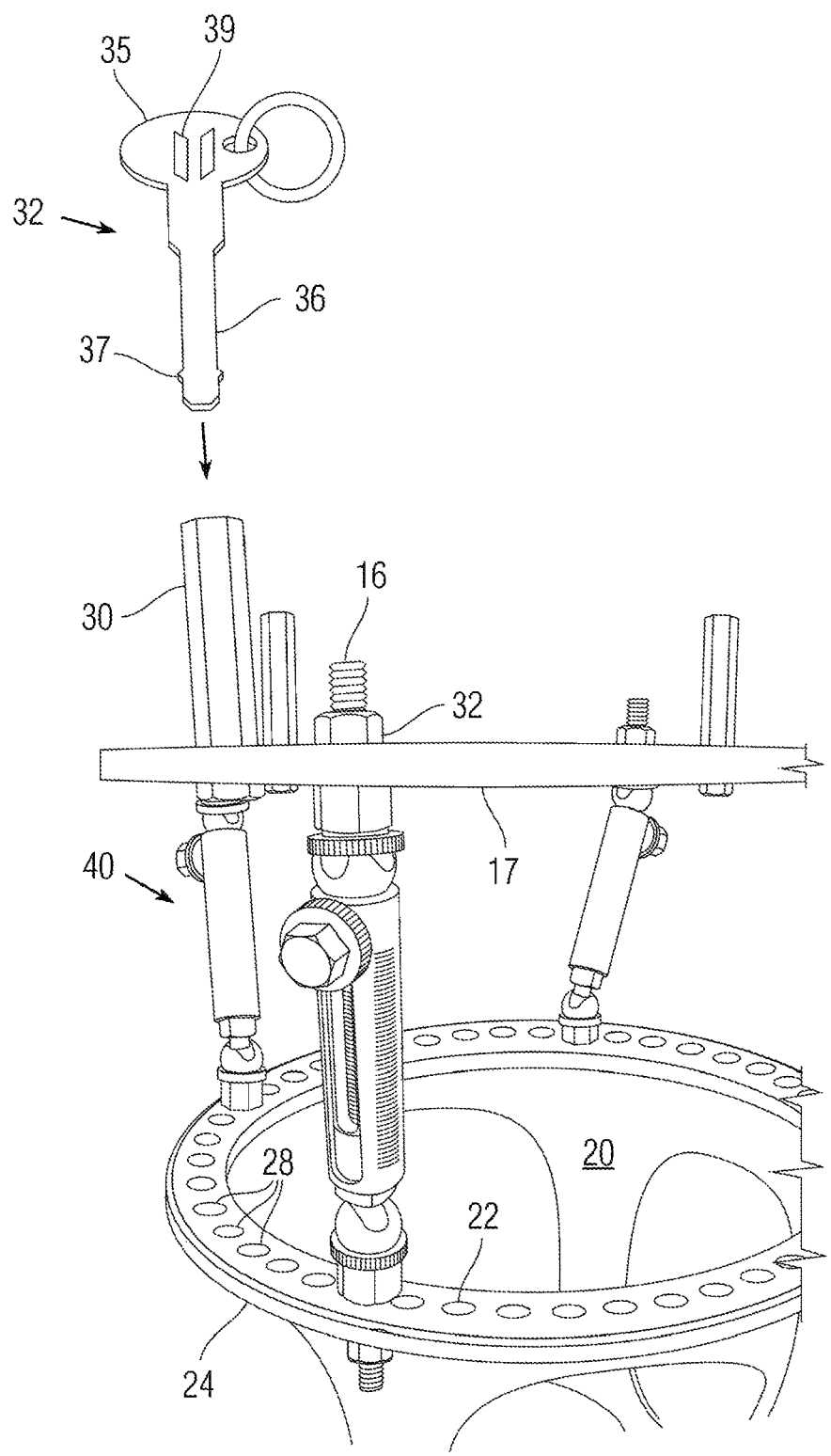
FIG. 3 is a close-up perspective illustration of the system 2 of FIGS. 1-2 adapted for quick-connect removable connection to an external ring fixator.

FIGS. 3-4 are perspective illustrations of the reducer 20. The reducer 20 is a coupling decreasing in diameter at one end configured for coupling any standard male or female adapters for attaching prosthetic limbs or feet (e.g., pyramid adapters). The illustrated reducer 20 comprises a shallow stump socket configured for enclosing all or part of the lower residual stump socket of an amputated limb. Toward this end reducer 20 is generally shaped as an open concave receptacle formed of rigid lightweight plastic with a closed end and an open end surrounded by an outwardly-flared circular rim 24. The outwardly-flared circular rim 24 is recessed to seat a reinforcing ring 24, which is a circular metal (e.g., aluminum) ring defined by equal angularly-spaced mounting holes. The rim 24 is reinforced by the ring 22 which is compression-fit and/or adhered therein.

Figure 5:
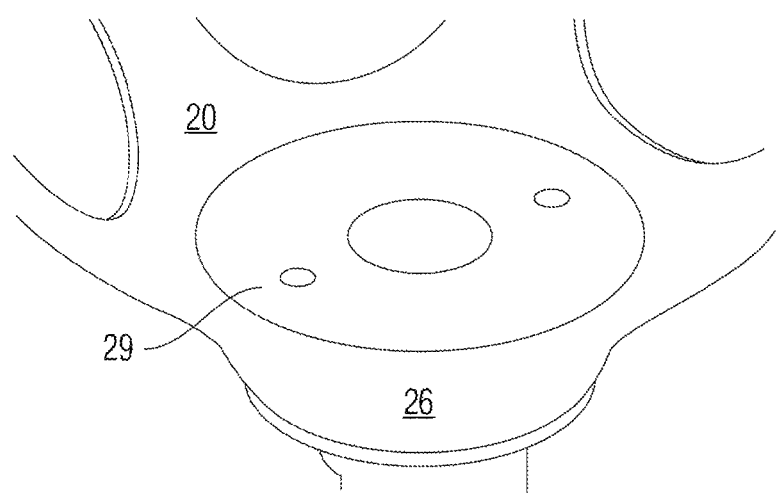
FIG. 5 is another close-up perspective illustration of the socket of FIG. 3.

The reducer 20 is most preferably formed of Kevlar™ or other fiber-reinforced plastic, but may alternatively be molded from, e.g., bisphenol A (BPA) plastic. As seen in FIG. 5 the reducer 20 is formed with a reinforced-thickness circular platform 26 at its apex, the platform 26 having an interior recess seating a circular silicon pad 29 for comfort and with surface features (annular ribs) for grip. The mounting base 32 for mounting prosthetic leg 50 and foot 60 is screw-attached exteriorly to the platform 26 (seen in FIG. 1). The base 32 may be any suitable prosthetic leg attachment base, such as a conventional prosthetic pyramid base adapted for attachment of a prosthetic leg 50 and foot 60 via a pyramid receiver, as is well-known in the art.

FIG. 3 is a close-up view of a quick-connect length-adjustable spacer 30 and quick-connect pin 32. The spacer 30 may be secured on one side of articulating ring 17 by the threaded end of strut 40 screwed therein through the other side of ring 17. Alternatively, the spacers 30 may be secured by separate bolts. Each spacer 30 is a tubular spacer having an internally-threaded receptacle on one end (bottom) and an internally smooth-bore receptacle on the other end (top). The internally-threaded end of receptacle 31 is screw-attached to the articulating ring 17, and the smooth-bore receptacle on the other end (top) is detachably attached to the lowermost ring 16 of the external ring fixation assembly 10 by a detent pin 32 that passes through the smooth-barreled metal spacer 30 and is anchored therein. As seen in FIG. 3, the detent pin 32 comprises an enlarged head 35 attached to an elongate cylindrical shaft 36. The shaft 36 terminates at a conical tip configured with a detent bearing 37. The detent bearing 37 may be released by depressing a thumb-button 39 in the head 35, thereby freeing the bearing 37 to recess inside the shaft 36, thereby allowing removal of the detent pin from spacer 30. Conversely, releasing the thumb-button locks the bearing 37 in place thereby locking the pin 32 in the spacer 30.

The distance of the reducer 20 from the external fixation assembly 10 and/or the offset angle of the prosthetic foot 60 (FIG. 1) may be adjusted by adjusting the length and/or pivot angles of the unidirectional-pivoting length adjustable struts 40. After use, the entire system 2 may be quick-released and removed from the external ring fixation assembly 10 (and the patient) by removing the quick-connect pins 32.

It should now be apparent that the foregoing system 2 is quickly attachable, fully adjustable, and allows the amputee patient to remain active and ambulatory almost immediately with minimal assistive devices, improving circulation and healing as well as psychological advantages.

Those skilled in the art will understand that various modifications and variations can be made in the present invention without departing from the spirit or scope of the invention. It is to be understood, therefore, that the invention may be practiced otherwise than as specifically set forth in the appended claims.

What is claimed is:

1. An apparatus for attachment of a prosthetic leg to an external ring fixation assembly, comprising:
   a reducer having an open circular rim at one end and tapering to a smaller coupling end;
   an adapter at the coupling end of said reducer configured for connection of a prosthesis; and
   a coupling mechanism comprising a plurality of struts attached at one end by locking-pivot-joints to the circular rim of said reducer and attached at another end to an articulating ring, said articulating ring being configured for connection to said external ring fixation assembly.

2. The apparatus according to claim 1, wherein said external ring fixation assembly is configured for bone fixation.

3. The apparatus according to claim 2, wherein said coupling mechanism comprises a plurality of struts each attached to and angularly adjustable relative to the rim of said reducer.

4. The apparatus according to claim 3, wherein said plurality of struts are each length-adjustable.

5. The apparatus according to claim 1, wherein said reducer comprises a rigid recessed socket having an open rim at one end and tapering to said smaller coupling end.

6. The apparatus according to claim 1, further comprising a reinforcing ring attached to the rim of said reducer and said coupling mechanism comprises quick-release pins attached to said articulating ring for quick-release connection to said external ring fixation assembly.

7. The apparatus according to claim 6, wherein said plurality of struts are each attached at one end by locking-ball-joints to the circular rim of said reducer and are omni-angularly-adjustable relative to the reinforcing ring.

8. The apparatus according to claim 7, wherein each of said plurality of adjustable struts is length-adjustable.

9. The apparatus according to claim 1, wherein said reducer comprises a fiber-reinforced composite socket.

10. An apparatus for attachment of a prosthetic leg to an external ring fixation assembly, comprising:
    a rigid base having an open circular rim at one end and tapering to a smaller coupling end configured for connection of a prosthesis; and
    a coupling mechanism comprising a plurality of struts attached at one end by locking-joints to the open circular rim of said base and attached at another end to an articulating ring, said articulating ring being configured for connection to said external ring fixation assembly.

11. The apparatus according to claim 10, wherein said external ring fixation assembly is configured for bone fixation.

12. The apparatus according to claim 10, wherein said base comprises a reducer.

13. The apparatus according to claim 12, wherein said reducer comprises a rigid recessed socket having an open rim at one end and tapering to said smaller coupling end.

14. The apparatus according to claim 13, wherein said coupling mechanism comprises a plurality of struts each attached at one end by locking-pivot-joints to the rim of said socket and configured for omni-angular adjustment relative to the rim of said socket.

15. The apparatus according to claim 14, wherein said plurality of struts are each length-adjustable.

16. An apparatus for removably-connecting a prosthesis to an external bone fixation assembly, comprising:
    a reducer having an open rim at one end and tapering to a smaller coupling end configured for mounting an adapter for connection of a prosthesis;
    a mounting mechanism comprising a plurality of struts each attached at one end by locking-joints to the rim of said reducer and attached at another end to an articulating ring, said articulating ring being configured for quick-release connection to said external bone fixation assembly, said plurality of struts being configured both for angular adjustment and length adjustment.

17. The apparatus according to claim 16, wherein said mounting mechanism further comprises a plurality of spacers attached to a ring.

18. The apparatus according to claim 17, wherein each of said plurality of adjustable struts is attached between the rim of said reducer and said articulating ring.

19. The apparatus according to claim 17, wherein each of said plurality of spacers comprises a receptacle attached to said ring and a quick-release pin.

20. The apparatus according to claim 16, wherein said reducer comprises a fiber-reinforced composite socket.

* * * * *